US006326394B1

United States Patent
Schmitt et al.

(10) Patent No.: US 6,326,394 B1
(45) Date of Patent: *Dec. 4, 2001

(54) CALIXARENE TUBES AS CATION RECEPTORS

(75) Inventors: Philippe Schmitt, Lyons (FR); Paul D Beer, Oxford (GB)

(73) Assignee: The Secretary of State for Defence in Her Britannic Majesty's Government of the United Kingdom of Great Britain and Northern Ireland, Whitehall (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/446,458
(22) PCT Filed: Jun. 24, 1998
(86) PCT No.: PCT/GB98/01854
  § 371 Date: Jun. 30, 2000
  § 102(e) Date: Jun. 30, 2000
(87) PCT Pub. No.: WO99/00394
  PCT Pub. Date: Jan. 7, 1999

(30) Foreign Application Priority Data

Jun. 25, 1997 (GB) .................................................. 9713292

(51) Int. Cl.[7] ........................ A61K 31/335; C07D 321/00
(52) U.S. Cl. ...................... 514/450; 549/348; 502/150; 502/172; 204/416
(58) Field of Search ........................ 549/348; 514/450; 502/172, 150; 204/416

(56) References Cited

FOREIGN PATENT DOCUMENTS

WO 94 12502 A  6/1994 (WO) .
WO 94 24138 A  10/1994 (WO) .

OTHER PUBLICATIONS

Derwent Publications Ltd, AN 94–273708 & JP 06 201639, Jul. 22, 1994.
Gokel et al, "synthetic Organic Chemical Models for Transmembrane Channels", *Accounts of Chemical Research*, vol. 29, No. 9, 1996, pp. 425–432.

Ghidini et al, "Complexion of Alkali Metal Cations by Conformationally Rigid, Steroisomeric Calix[4]arene Crown Ethers: A Quantitative Evaluation of Preorganization", *American Chemical Society*, vol. 112, No. 19, 1990, pp. 6979–6985.

King et al, "A Highly Selective Chromoinophore for Potassium Based upon a Bridged Calix[4]arene" *Journal of the Chemical Society, Chemical Communications*, 1992, pp. 582–584.

*Primary Examiner*—Amelia Owens
(74) *Attorney, Agent, or Firm*—Nixon & Vanderhye

(57) ABSTRACT

A cyclic compound of formula (I)

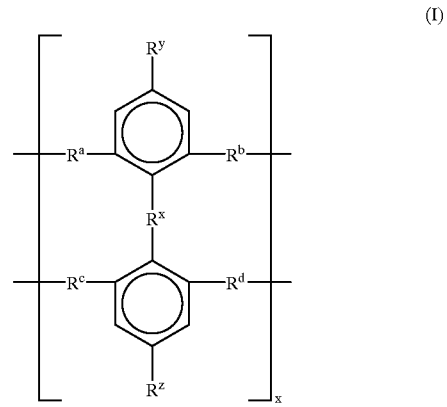

wherein $R^x$ groups which may be the same or different are selected from $-O-(CH_2)_n-O-$ where n is an integer of from 2–6; $R^y$ and $R^z$ groups which may be the same or different are independently selected from hydrogen, halogen or a hydrocarbyl group; $R^a$ together with $R^b$ of the adjacent phenyl ring and $R^c$ together with $R^d$ of the adjacent phenyl ring form a group of formula $-(CH_2)_m-$ or $-(CH_2)_p-O-$ where m and p are integers of from 1–5, and each group $R^a-R^b$ and $R^c-R^d$ may be the same or different; and x is an integer of 2 or more, such as 4. Compounds of formula (I) display particular selectivity for specific ions such as potassium ions. They are useful inter alia in reactions where scavenging of a specific cation is required or as ion specific electrodes.

15 Claims, 4 Drawing Sheets

CALIXARENE TUBES AS CATION RECEPTORS

The present invention relates to molecules which are specific for certain cations, such as potassium or caesium, to their preparation and their uses for example as reagents in reactions requiring a cation scavenging agent. The molecules of the invention which are specific for potassium ions may also be regarded as mimicing potassium ion channels Potassium channel proteins have been the subject of an intense investigation this last decade and a great deal of information about their structure/function relationships has been elucidated (e.g: C. Miller, *Science* 1991, 252, 10921096 (re-view), J. O. Dolly, et al., J. Bioenerg. Biomembr. 1996, 28, 231–253; Q Lüet al., Science 1995, 268, 304–307; P. Hidalgo et al., Science 1995,268, 307–310; J. Aiyar, et al., Neuron 1995, 15, 1169–1181; M. Stocker et al., Proc. Natl. Acad. Sci. USA 1994, 91, 9509–9513; J. C. Bradley et al., Protein Eng. 1993, 7, 859–862). A very exciting aspect, still controversial, focuses on how these proteins transport potassium through the cell membrane, with high rates and almost perfect selectivity (K+ transported 1000 times more efficiently than Na+) (G. Yellen, J. Gen. Physiol. 1984, 84, 157; J. Neyton et al. J. Gen. Physiol. 1988, 92, 569).

The channel pore region responsible for the crucial alkali-metal selection, termed the selection filter, contains a square planar array of four converging tyrosine residues (e.g. R. Ranganathan et al., Neuron 1996, 16, 131–139; L. Heginbotham et al., Biophys. J. 1994, 66, 1061–1067; S. Bogusz et al., Protein Eng. 1992, 5, 285–293). A proposed selection mechanism, supported by experimental and ab initio studies, suggests that an en face cation-π interaction between the potassium and the aromatic surfaces of the tyrosines could be determinant for such a unique selectivity pattern (D. A. Dougherty, *Science* 1996, 271, 163–168; C. Miller, Science 1993, 261, 1692–1693; L. Heginbotham, et al., Neuron 1992, 8, 483–491; J. Sunner et al., J. Phys. Chem. 1981, 85, 1814–1820).

Despite the involvement of numerous research groups in the development of synthetic channels (reviewed by G. W. Gokel et al., Acc. Chem. Res. 1996, 29, 425–432; K. S. Akerfeldt et al., Acc. Chem. Res. 1993. 26, 191–197, a biomimetic approach focusing in particular on the alkali-metal selection process has not previously been fully investigated. In an effort to accredit the cation-π hypothesis, a novel biomimetic calix[4]arene based tubular receptor whose access to metal cations may be controlled by filtering gates based on a square planar array of aromatic surfaces was designed.

According to the present invention, there is provided a cyclic compound of formula (I)

(I)

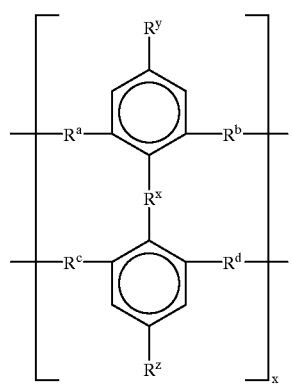

wherein $R^x$ groups which may be the same or different are selected from

—O—$(CH_2)_n$—O— or —O—$(CH_2CH_2O)_n$— where n is an integer of from 2–6:

$R^y$ and $R^z$ groups which may be the same or different are independently selected from hydrogen, halogen or an optionally substituted hydrocarbyl group;

$R^a$ together with $R^b$ of the adjacent phenyl ring and $R^c$ together with $R^d$ of the adjacent phenyl ring form a group of formula —$(CH_2)_m$— or —O—$(CH_2)_p$—O— where m and p are integers of from 1–5, and each group $R^a$–$R^b$ and $R^c$–$R^d$ may be the same or different; and x is an integer of 4 or more.

Suitably x is an integer of from 4–8. The precise number of x will depend upon the ion which the compound of formula (I) is intended to be specific for. In the case of potassium, x is suitably 4, but for caesium a higher value, for example 5 may be preferred.

Thus in a preferred embodiment, the invention provides a compound of formula (II)

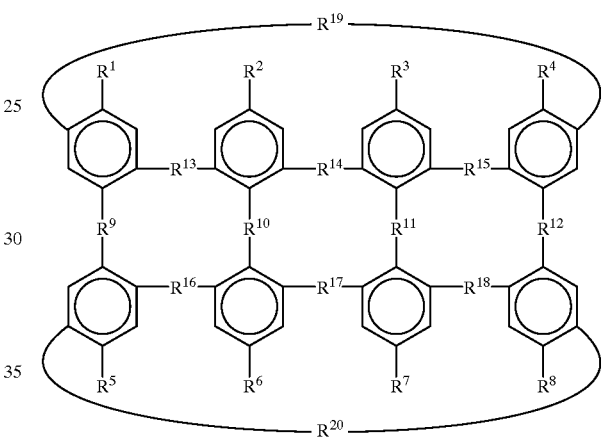

where $R^1$, $R^2$, $R^3$, $R^4$, $R^5$, $R^6$, $R^7$, and $R^8$ are independently selected from hydrogen, halogen, or an optionally substituted hydrocarbyl group;

$R^9$, $R_{10}$, $R^{11}$ and $R^{12}$ are independently selected from —O—$(CH_2)_n$—O— where n is an integer of from 2–6;

$R^{13}$, $R^{14}$, $R^{15}$, $R^{16}$, $R^{17}$, $R^8$, $R^{19}$ and $R^{20}$ are independently selected from —$(CH_2)_m$— or —O—$(CH_2)_p$—O— where m and p are integers of from 1–5.

Suitable hydrocarbyl groups for $R^y$, $R^z$, $R^1$, $R^2$, $R^3$, $R^4$, $R^5$, $R^6$, $R^7$ and $R^8$ include hydrocarbyl groups containing from 1 to 20 carbon atoms including straight or branched alkyl, alkenyl or alkynyl groups, cycloalkyl, aryl groups or aralkyl groups. As used herein, the term 'aryl' includes phenyl and naphthyl groups. The term "aralkyl" includes $C_{1-6}$alkylaryl such as benzyl. Suitable optional substitutents for hydrocarbyl groups include functional groups such as ether or ester groups, in particular alkyl ether or ester groups.

Preferably $R_1$, $R^2$, $R^3$, $R^4$, $R^5$, $R^6$, $R^7$ and $R^8$ are the same group, in particular $C_{1-6}$alkyl groups such as methyl, ethyl, propyl or n- or tert-butyl, most preferably tert-butyl.

Suitably $R^9$, $R^{10}$, $R^{11}$ and $R^{12}$ are the same and n is 2.

Suitably $R^{13}$ $R^{14}$, $R^{15}$, R , $R^{16}$, $R^{17}$, $R^{18}$, $R^{19}$ and $R^{20}$ are the same group, in particular an alkylene group where m is 1.

Preferably p is 1.

Compounds of formula (I) are suitably prepared by reacting a compound of formula (III)

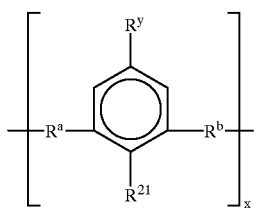

(III)

where $R^y$, $R^a$, $R^b$ and x are as defined in relation to formula (I), and and $R^{21}$ groups are the same or different and are selected from —O—$(CH_2)_n$—O—$R^{22}$ where $R^{22}$ is a leaving group such as tosylate or mesylate;

with a compound of formula (IV)

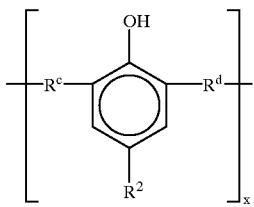

(IV)

where $R^z$, $R^c$, $R^d$ and x are as defined in relation to formula (I); in the presence of a base.

Suitable bases include weak bases such as carbonates, in particular alkali metal carbonates such as potassium carbonate.

Suitably the reaction is effected in the presence of an organic solvent such as acetonitrile.

Compounds of formula (III) and (IV) are either known compounds or they can be prepared from known compounds by conventional methods.

For example, the template-driven condensation of p-tert-butyl-calix[4]arene (VI) with a per-tosylated derivative of formula (V) in acetonitrile, in presence of potassium carbonate, furnished the novel calix[4]tube (VII) in fairly good yields (51% isolated yields, Scheme 1).

Scheme I

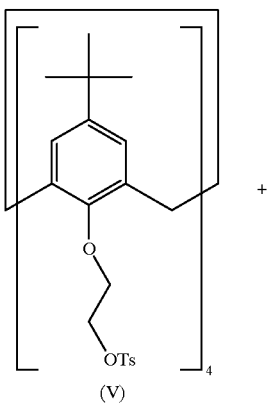

+

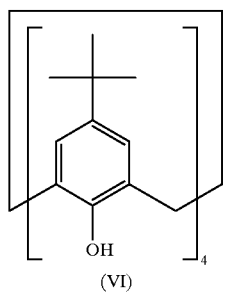

(VI)

$CH_3CN$, $K_2CO_3$; 51%

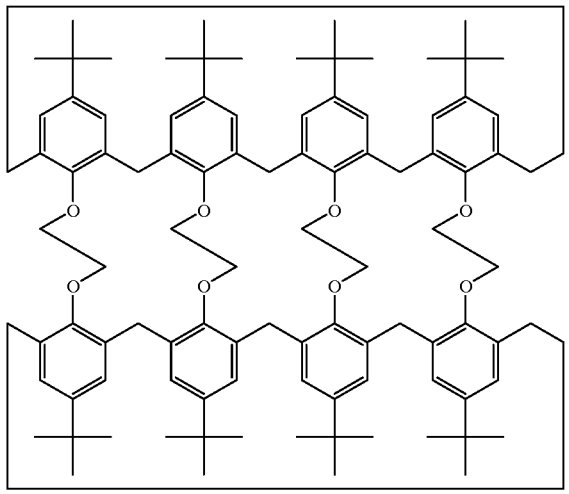

(VII)

Compounds of formula (I) combine several appealing features that make them a suitable model system of relevance for the design of new selective ion channels in particular potassium selective ion channels as illustrated hereinafter. They may be utilised in an in vitro screen, where compounds which have an effect on potassium ion channels would be of assistance. In addition, the effects on cell membranes may mean that compounds of formula (I) display antibiotic properties.

Moreover, the amazing potassium selectivity displayed by compound VI, allied with the biomimetic design of its cation-accessing gates, tend to accredit the cation filtering role occupied by the fourfold symmetrical array of aromatic residues at the narrower portion of naturally occurring channels. The distance separating the two cofacial phenyl rings in compound VI (5.88 Å) is very close to the corresponding distance, predicted by ab initio calculations, in a hypothetical cation-π complex -(bis-$\eta^6$-arene) made of two benzene rings and a potassium ion (5. 84 Å) (R. A. Kumpf, D. A. Dougherty, Science 1993, 261, 1708–1710). This raises the question as to whether such a transient species between compound VII and K+, may be responsible for the very original binding behaviour observed.

These properties mean that the compounds of the invention may also be utilised as ion selective electrodes which select specifically particular ions such as potassium ions. Such electrodes form a further aspect of the invention.

In addition, the compounds of formula (I) can be used as a reagent in chemical reactions and processes where cation scavenging is required. Such reactions include the purification of analar salts of alkali and alkaline earth metals. For instance, contact of sodium, lithium and caesium salts with compound of formula (II) will result in the removal of contaminating potassium ions.

Furthermore, compounds of formula (I) may act as phase transfer catalysts. Addition of compounds of formula (I) to organic synthesis reactions may result in the solubilisation of specific salts.

The invention will now be particularly described by way of example with reference to the accompanying diagrammatic drawings in which

EXAMPLE 1

Preparation of Potassium Ion Selective Calixarene

A suspension of p-tert-butyl-calix[4]arene (451 mg, 0.70 mmol) and potassium carbonate (480 mg, 3.5 mmol) in 100 ml of dry acetonitrile was stirred under nitrogen. After 2 hours at room temperature, compound V (1 g, 0.70 mmol) was added and the reaction mixture brought to reflux for 5 days. The solvent was then removed in vacuo and the solid suspended in a 1:1 ethanol-water mixture. The suspension was refluxed overnight and hot filtered. The crude mixture was then dissolved in 50 ml of chloroform and carefully paper filtered to yield a clear solution to which 40 ml of acetone was added. The filtration of the microcrystalline material obtained after a few hours of standing, followed by its drying in vacuo yields 500 mg of compound VII as an analytically pure product (51%). $^1$H NMR (500 MHz, $CDCl_3$): δ=7.09 (s, 8H, H, H1/H1'), 6.48 (s, 8H⁻, H1/H1'), 5.15 (s, 8H, H2/H2'), 4.57 (d, j=13 Hz, 8H, H3), 4.39 (s, 8H, H2/H2'), 3.25 (d, j=13 Hz, 8H, H4), 1.31 (s, 36H, H5/H5'), 0.80 (s, 36H, HS/H5'); $^{13}$C NMR (125 MHz, $CDCl_3$): δ=156.0 (C1/C1'), 152.8 (C1/C1'), 144.5 (C2/C2'), 144.3 (C2/C2'), 135.1 (C4/C4'), 131.9 (C4/C4'), 125.5 (C3/C3'), 124.8 (C3/C3'), 73.0 (C5/C5'), 72.5 (C5/C5'), 34.1 (C6/C6'), 33.5 (C6/C6'), 32.4 (C8), 31.7 (C7/C7'), 31.0 (C7/C7.');

C,H,Cl-analysis ($C_{96}H_{120}O_8 \cdot CHCl_3$): calc. C, 76.58; H, 8.02; Cl, 6.99. found: C, 76.32; H, 8.17; Cl 8.09.

Figure 1:
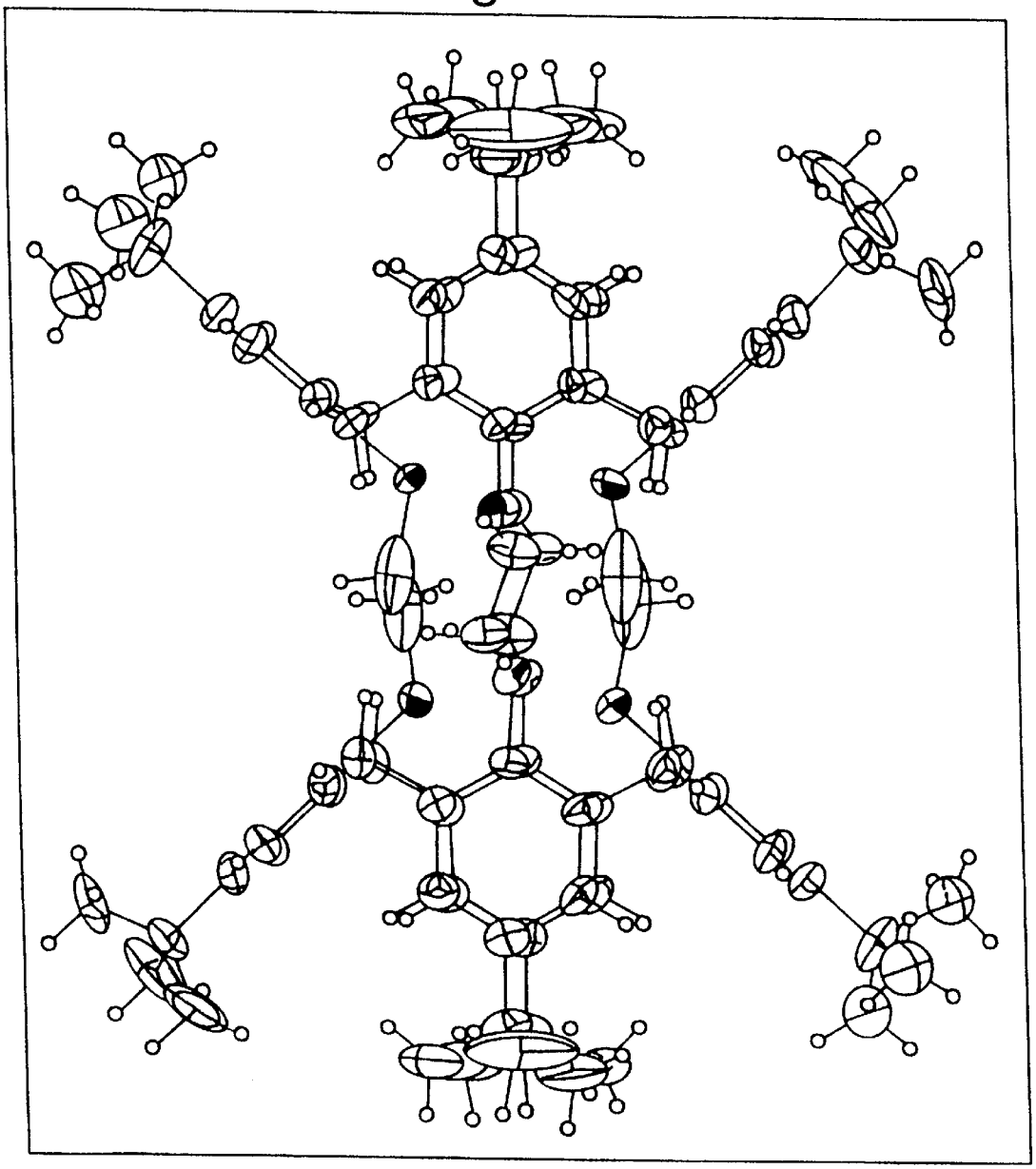
FIG. 1 is an ORTEP view of a compound of the invention (compound VII) based on X-ray crystal structure analysis.

Surprisingly the compound of formula (VII) was found to be insoluble in all common organic solvents with the exception of chloroform and carbon tetrachloride. Crystallized from a chloroform/benzene mixture, compound (VII) was submitted to crystal structure analysis (FIG. 1) and found to exhibit a $C_i$ symmetry in the solid state. The crystal structure data is as follows:

Triclinic, P 1, a=10.286(12), b=14.803(14), c=19.01(2) Å, α=75.705(10), β=83.663(10), γ=64.910(10)°, V=2541 (5) Å, z=1, λ($Mo_{Kα}$)=0.71073 Å, T=293(2)° K. 7510 independent reflections were measured on a MAR-research Image Plate up to 2θ=25.09°. Data a analysis was carried out with the XDS program ( . . . ). The structure was solved with directs methods and anisotropically refined on $F^2$ (program SHELX-86, G. M. Sheldrick, Universität Göttingen).

It contains two identical flattened calix[4]arene units each of which consists of two almost parallel, and two almost perpendicular phenyl rings. It is noteworthy that the ethylene linkages alternate in two different geometries. Two of them present an anti-like conformation (O—C—C—O torsion angle of 162.2° whereas the remaining two display a gauche-type conformation (O—C—C—O torsion angle of 47.80°. As a consequence of this particular arrangement, the central eight oxygen cage is unsuitable to form an inclusion complex.

Interestingly, on the NMR time-scale, this conformational symmetry was mostly conserved in solution. Dissolved in deuterated chloroform, compound (VII) exhibited both $^1$H and $^{13}$C NMR spectra consistent with the freezing of the calixarenes in their-flattened cone conformation. With the exception of the methylene related peaks, all the signals were found split in two sinalets of equal intensity. Moreover, up to 55° C. the $^1$H-NMR spectra were found to be temperature independent. The absence of any coalescence or even peak broadening, features indicative of a time-averaged $D_{4h}$ symmetry, suggests that a calix[4]tube is an extremely rigid molecule in solution. As a consequence of the solubility limitations of compound VII, a deuterated chloroform-methanol (8:2) mixture was employed for the NMR-based metal cation complexation studies. To 1ml of compound VII in this solvent mixture (1 mM) at 25° C. was added 10pmol (10 μmol (10 equivalents of solid alkali-metal iodide. The samples were sonicated briefly and $^1$H-NMR spectra were recorded at various times.

EXAMPLE 2

Reaction with Alkali Metals

Figure 2:
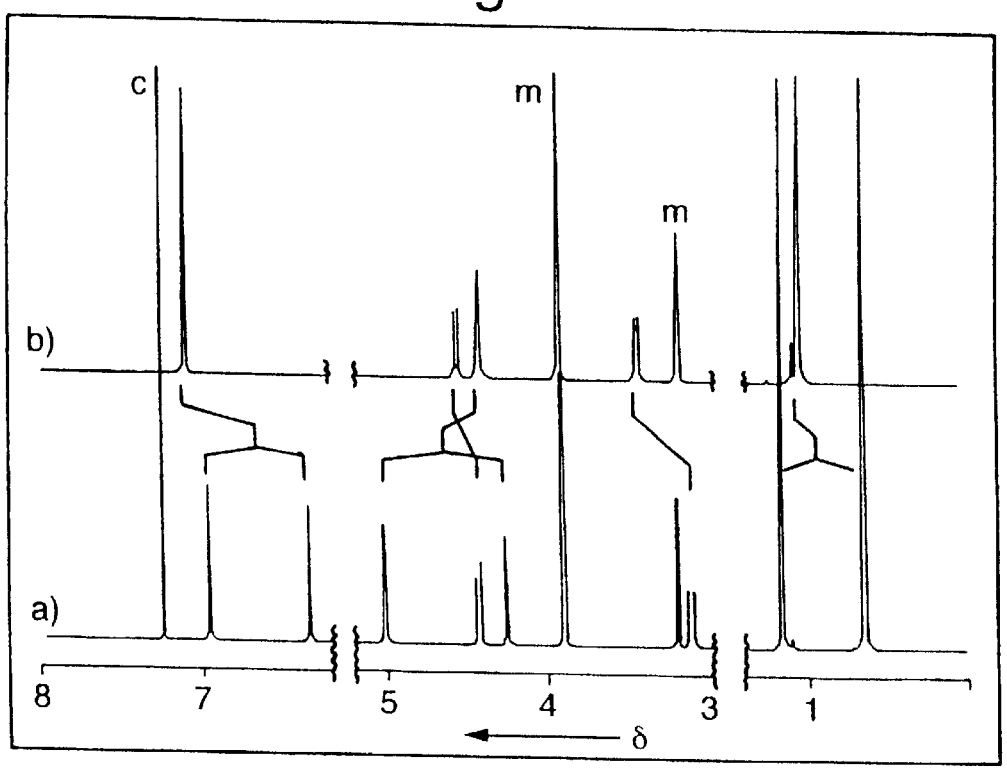
FIG. 2 shows $^1$H NMR spectrum of compound VII [500 MHz, $CDCl_3$—$CD_3OD$ 4/1 (v/v)]: a) pure compound VII, b) with 10 equivalent of solid potassium iodide (c,m: solvent peaks corresponding respectively to chloroform and methanol)

A chloroform-methanol solution (4/1, compound VII=1 mM) with 10 equivalents of various alkali metal iodides. Treated with potassium iodide, compound VII underwent a dramatic change to a potassium complex compound VIII. Within the first hour upon mixing the initial spectrum disappeared below detection and was replaced by a new set of peaks suggestive of an increase of the ligand symmetry (FIG. 2). The structural degeneracy of compound VII, characterized by a fourfold symmetry along the molecule's main axis, is consistent with the opening of the binding cavity driven by the complexation of potassium cation within the eight oxygen-cage.

Figure 3:
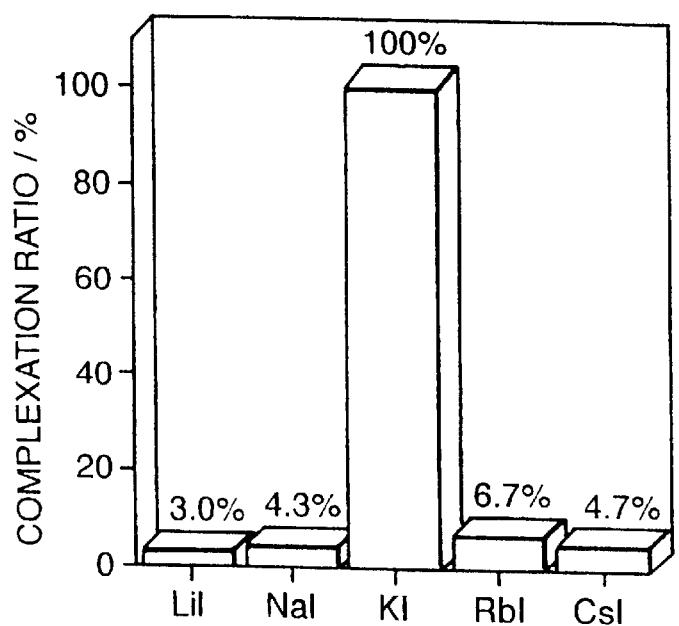
FIG. 3 shows the results of monitoring the metallic untake of compound VI by treating its chloroform-methanol solution (4/1, compound VII=1 mM) with 10 equivalents of alkali-metal iodide. The measurements were made by relative integration of the corresponding $^1$H-NMR spectra after 90 hours (3.7 days) of standing. In the case of KI, equilibrium was reached within an hour.

Analogous experiments with other alkali-metal iodides (LiI, NaI, RbI and CsI) failed to exhibit any significant cation uptake. Estimated by relative integration, less than 7% of compound VII was complexed after more than three days in presence of 10 equivalents of RbI. This ratio dropped below 5% in the cases of LiI, NaI and CsI (FIG. 3). Although synthetic ionophores displaying a high potassium selectivity are known (E. Ghidini et al., J. Am. Chem. Soc. 1990, 112, 6979–6985; A. M. King et al., J. Chem. Soc. Chem. Commun. 1992, 582–584) such a remarkable preference for potassium over any of the alkali-metals is unprecedented for a synthetic receptor.

EXAMPLE 3

Investigation of Potassium Complexation

In order to investigate the potassium complexation process quantitatively, the uptake of 1 μmol of KI ([K1]=10-3 M) by one equivalent of compound VII, in homogeneous solution at 25° C., was monitored as a function of time. After 24 hours the system was evaluated to have reached equilibrium (86% of compound VI was complexed), the formation of a 1:1 complex was established and a stability constant of 4×10⁴ L mol-1 was estimated. The complexation halftime, defined by the time necessary for the system to reach half the equilibrium conversion ratio, was measured to be 18 minutes. Although these are preliminary results, this experiment reveals the complexation process is kinetically slow and may be a consequence of an important intramolecular reorganization necessary for the cation uptake.

Comparison of the chemical shifts values of compound VII and of its potassium complex, shows in general low-field shift deviations of all the calix[4]arene-related signals (Δδ tert-butyl:+0.923 ppm, phenyl: 0.426 ppm, methylene:+ 0.216 ppm), whilst the ethylene protons exhibit an average high field variation in their corresponding signals (−0.228 ppm, FIG. 2). This feature is consistent with a displacement of the ligand electron density towards the molecule's equatorial plane caused by the close proximity of the complexed metal positive charge.

Figure 4:
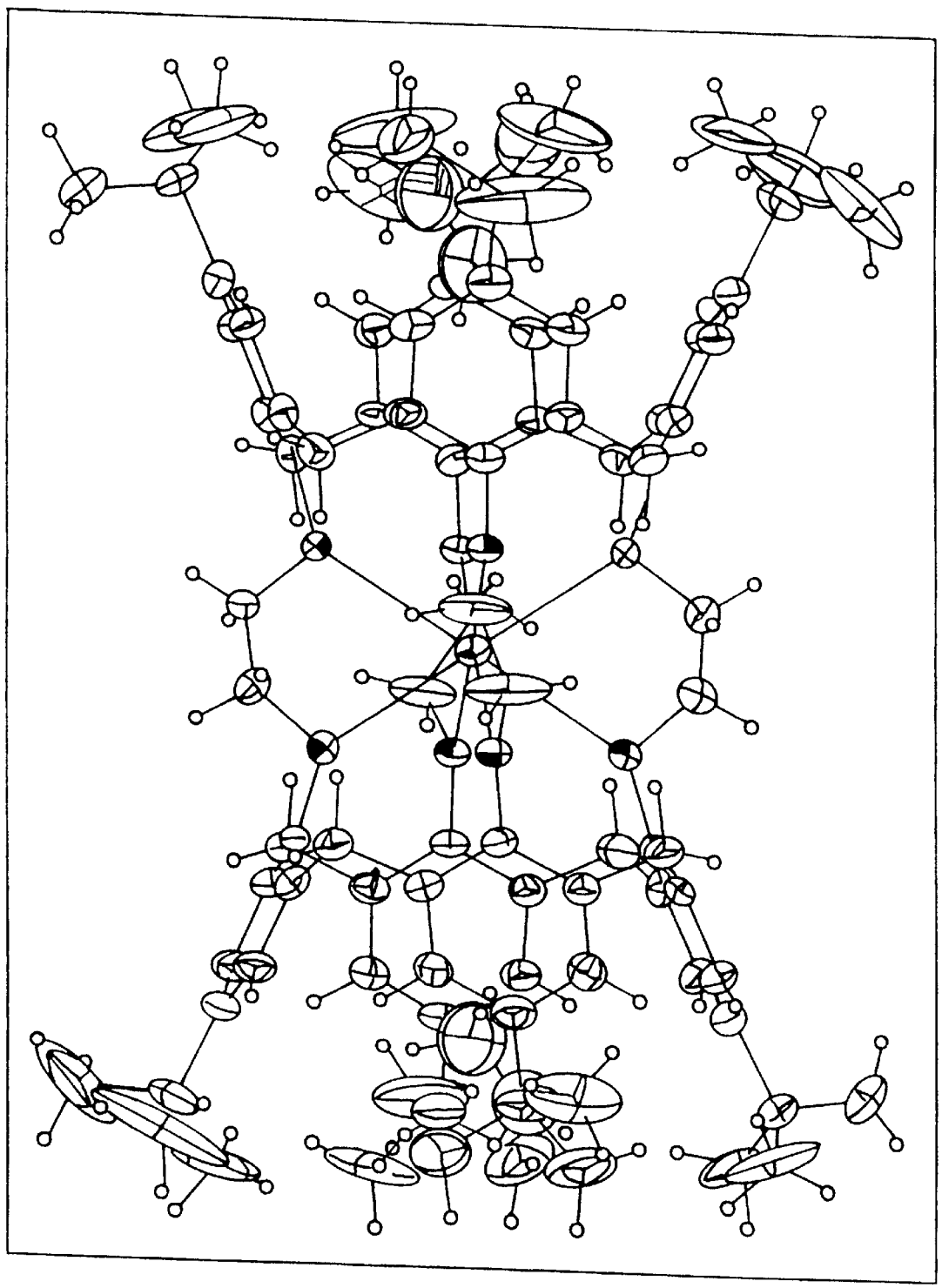
FIG. 4 is an ORTEP view of compound (VIII) which is the potassium complex of compound VII based on X-ray crystal structure analysis.

The geometry of the complex VIII was confirmed by X-Ray analysis. As predicted by NMR, compound VIII is highly symmetrical and contains a $C_4$ along the main axis of the molecule ($D_4$ point group). The potassium atom is located at the centre of a slightly flattened cube at an average distance of 2.78 Å from all oxygen atoms (FIG. 4).

EXAMPLE 4

Molecular Dynamics Studies

Figure 5:
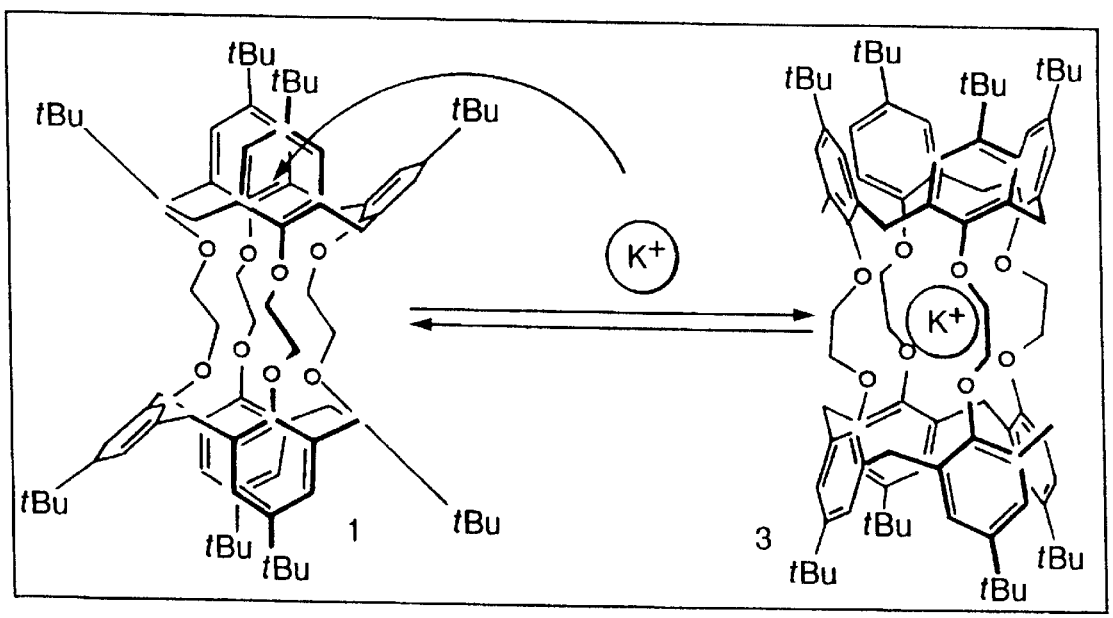
FIG. 5 is a schematic representation of the potassium uptake of compound VII based on molecular dynamics calculations.

Of relevance to potassium selective channel transportation, it is worthwhile speculating as to how the potassium cation enters the oxygen cage cavity of calix[4] tube. Examination of both solid-state structures suggests that the calix[4]arene macrocycles would form the main accesses to the potassium-binding site (FIG. 5). Even though known for monomeric calix[4]arenes, (P. Guibauld, et al., J. Am. Chem. Soc. 1993, 115, 8298–8312) this assumption was verified in the particular case of compound VII by ab initio molecular dynamics (Quanta, CHARMM version 23.1, Molecular Simulations Inc., Cambridge UK, San Diego, Calif. USA). Preliminary modellings suggested indeed that the complexation of potassium would require an activation energy 10 to 15 kcal mol⁻¹ larger by accessing the cavity across rather than along the main axis.

What is claimed is:

1. A cyclic compound of formula (I)

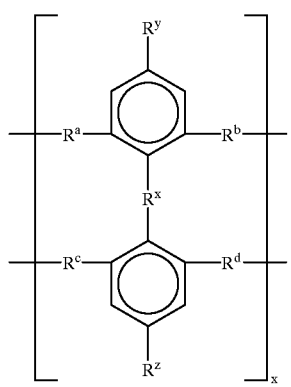

formula (I)

wherein $R^x$ groups which may be the same or different are selected from —O—(CH₂)ₙ—O— or —O—(CH₂CH₂O)ₙ— where n is an integer of from 2–6;

$R^y$ and $R^z$ which may be the same or different are independently selected from hydrogen, halogen or a straight or branched alkyl, alkenyl or alkynyl group, a cycloalkyl, aryl or aralkyl group containing up to 20 carbon atoms, said group optionally substituted with an ether or an ester group;

$R^a$ together with $R^b$ of the adjacent phenyl ring and $R^c$ together with $R^d$ of the adjacent phenyl ring form a group of formula —(CH₂)ₘ— or —O—(CH₂)ₚ—O— where m and p are integers of from 1–5, and each group $R^a$-$R^b$ and $R^c$-$R^d$ may be the same or different; and;

x is an integer of 4 or more.

2. The compound according to claim 1 wherein x is an integer of from 4–8.

3. The compound according to claim 1 of formula (II)

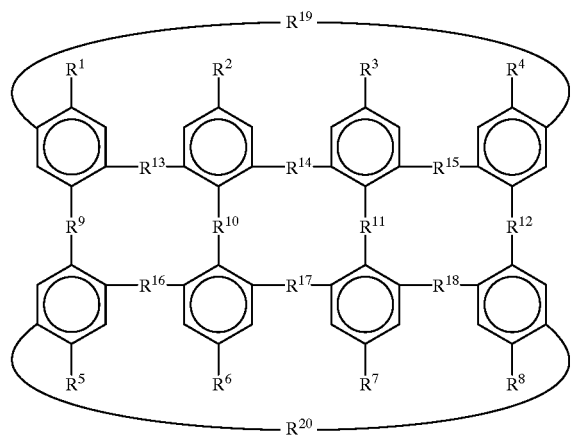

where $R^1$, $R^2$, $R^3$, $R^4$, $R^5$, $R^6$, $R^7$ and $R^8$ are independently selected from hydrogen, halogen or a straight or branched alkyl, alkenyl or alkynyl group or a cycloalkyl, aryl or aralkyl group;

$R^9$, $R^{10}$, $R^{11}$ and $R^{12}$ are independently selected from —O—(CH₂)ₙ—O— where n is an integer of from 2–6; and $R^{13}$, $R^{14}$, $R^{15}$, $R^{16}$, $R^{17}$, $R^{18}$, $R^{19}$ and $R^{20}$ are independently selected from —(CH₂)ₘ— or —O—(CH₂)ₚ—O— where m and p are integers of from 1–5.

4. The compound according to claim 3 wherein $R^1$, $R^2$, $R^3$, $R^4$, $R^5$, $R^6$, $R^7$ and $R^8$ are the same group.

5. The compound according to claim 3 wherein $R^1$, $R^2$, $R^3$, $R^4$, $R^5$, $R^6$, $R^7$ and $R^8$ are $C_{1-6}$ alkyl groups.

6. The compound according to claim 3 wherein $R^1$, $R^2$, $R^3$, $R^4$, $R^5$, $R^6$, $R^7$ and $R^8$ are tert-butyl.

7. The compound according to claim 3 wherein $R^9$, $R^{10}$, $R^{11}$ and $R^{12}$ are the same and n is 2.

8. The compound according to claims 3 wherein $R^{13}$, $R^{14}$, $R^{15}$, $R^{16}$, $R^{17}$, $R^{18}$, $R^{19}$ and $R^{20}$ are the same group.

9. A process for preparing a compound of formula (I) as claimed in claim 1 which process comprises reacting a compound of formula (III)

formula (III)

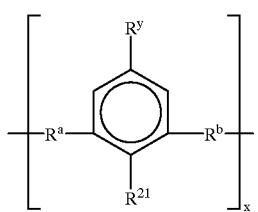

where $R^y$, $R^a$, $R^b$ and x are as defined in relation to formula (I), and $R^{21}$ groups are the same or different and are selected from —O—(CH$_2$)$_n$—O—R$^{22}$ where $R^{22}$ is a leaving group; with a compound for formula (IV)

formula (IV)

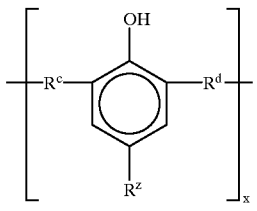

where $R^z$, $R^c$, $R^d$ and x are as defined in relation to formula (I); in the presence of a base.

10. The compound according to claim 8 wherein $R^{13}$, $R^{14}$, $R^{15}$, $R^{16}$, $R^{17}$, $R^{18}$, $R^{19}$ and $R^{20}$ are —CH$_2$— or —OCH$_2$O—.

11. An antibiotic composition comprising a compound of claims 1 which displays antibiotic properties.

12. An ion selective electrode comprising a compound of claim 1.

13. A method of purifying a salt of an alkali metal which comprises contacting said salt with a compound of claim 1 which is specific for a different cation.

14. A phase transfer catalyst comprising a compound according to claim 1.

15. A method of solubilizing a salt in an organic synthesis reaction, which comprises adding to a reaction mixture a compound according to claim 1.

* * * * *